United States Patent
Caillat et al.

[11] Patent Number: 6,126,800
[45] Date of Patent: Oct. 3, 2000

[54] MICRO-SYSTEM WITH AN INTEGRATED CUVETTE FOR THE ANALYSIS OF LIQUIDS

[75] Inventors: Patrice Caillat, Echirolles; Gérard Ponthenier, Champagnier, both of France

[73] Assignee: Commissariat a l'Energie Atomique, Paris, France

[21] Appl. No.: 09/088,872

[22] Filed: Jun. 2, 1998

[30] Foreign Application Priority Data

Jun. 6, 1997 [FR] France .................................. 97-07047

[51] Int. Cl.$^7$ .................................................. G01N 27/26
[52] U.S. Cl. ........................ 204/400; 204/403; 204/412; 204/416
[58] Field of Search .................................. 204/400, 416, 204/418, 419, 403, 415, 412

[56] References Cited

U.S. PATENT DOCUMENTS

| | | | |
|---|---|---|---|
| 3,767,469 | 10/1973 | Flais et al. | 204/424 |
| 4,867,860 | 9/1989 | Siddiqi et al. | 204/416 |
| 4,902,400 | 2/1990 | Usami et al. | 204/426 |
| 4,974,592 | 12/1990 | Branco | 204/416 |
| 5,046,496 | 9/1991 | Betts et al. | 204/403 |
| 5,138,251 | 8/1992 | Koshishi et al. | 204/416 |
| 5,141,868 | 8/1992 | Shanks et al. | 204/403 |
| 5,194,134 | 3/1993 | Futata et al. | 204/426 |
| 5,284,568 | 2/1994 | Pace et al. | 204/416 |
| 5,290,420 | 3/1994 | Matson | 204/403 |
| 5,325,853 | 7/1994 | Morris et al. | 204/403 |
| 5,354,447 | 10/1994 | Uenoyama et al. | 204/403 |
| 5,393,399 | 2/1995 | Van Den Berg et al. | 204/415 |
| 5,611,902 | 3/1997 | Leader et al. | 204/415 |

FOREIGN PATENT DOCUMENTS

WO 90/01700  2/1990  WIPO.
WO 96/02001  1/1996  WIPO.

*Primary Examiner*—T. Tung
*Attorney, Agent, or Firm*—Anderson, Kill & Olick P.C.

[57] ABSTRACT

An analysis micro-system with integrated cuvette comprising:

a chip support (250) having at least one cuvette (252), at least one chip (210) arranged in each cuvette, the chip comprising analysis electrodes (212) and addressing electrodes (214), and connection means (258, 260, 262) to connect the addressing electrodes to at least one electrical apparatus external to the micro-system.

Conforming to the invention, the connection means comprise connection terminals (258) arranged on the support, outside the cuvette (252), and electrical links (260, 262) connecting the connection terminals (258) to the addressing electrodes.

Application to the analysis of chemical and biological products.

11 Claims, 3 Drawing Sheets

MICRO-SYSTEM WITH AN INTEGRATED CUVETTE FOR THE ANALYSIS OF LIQUIDS

DESCRIPTION

1. Technological Field

This invention relates to a micro-system with an integrated cuvette for the analysis of liquids.

The invention comes within the context of the development of analysis systems that include an electronic chip with a specific integrated circuit having been subjected to a particular finish which allows it to be used in a liquid environment so as to determine physical, chemical or biological characteristics of it.

By way of example, an analysis system with an electronic chip can be used as a glucose measuring device, as a blood analysis device and also as a biological sensor.

The biological sensors with an electronic circuit are used for example for antibody-antigen recognition or as a DNA—DNA probe.

2. State of the Prior Technology

The appended FIG. 1 shows in section and in a diagrammatic way, a chip 10 of a biological sensor such as is used for antibody-antigen recognition or as a DNA—DNA probe.

The chip 10 includes two electrodes called analysis electrodes 12a and 12b and addressing electrodes 14 only one of which is visible. It should be made clear that the chips for a biological sensor generally comprise a large number of analysis electrodes. These electrodes can be addressed electrically by corresponding addressing electrodes. Nevertheless, when the number of analysis electrodes is very large, the chip may include a multiplexed addressing system that allows all of the analysis electrodes to be addressed from a reduced number of addressing electrodes.

By the term addressing, one understands the making of an electrical link between one or more analysis electrodes and one or more electrodes called addressing electrodes generally arranged on the periphery of the chip. The addressing electrodes permit the application of or the measuring of a voltage on the analysis electrodes, by means of an appropriate external apparatus.

For reasons of simplification, only two analysis electrodes are shown on the chip 10 in FIG. 1.

The analysis electrodes 12a and 12b are made of a metal such as, for example gold or platinum. They are insulated from one another on a substrate wafer 16. The electrical links between the analysis electrodes 12a, 12b and the addressing electrodes are arranged in the substrate 16 and are indicated very schematically by reference number 18.

A chip such as that shown in FIG. 1, must be configured for a particular use and the analysis electrodes are, to this end made operational by lining them with probe molecules or by covering their surface with a deposit of appropriate reactant.

The deposition of reactant products or the grafting of probe molecules onto the electrodes is carried out generally by electro-deposition.

The reactants or probe molecules deposited on the electrodes permit selective matching with specific molecules of a substance to be analysed. These molecules are called "target molecules" in the rest of the text.

FIG. 2 shows the chip 10 submerged in a bath of electrolyte 20. By bath of electrolyte, one understands a bath suitable for the deposition, by electrochemical means, of a reactant onto the electrodes, or a bath in which probe molecules are diluted before being fixed by electro-deposition onto the electrodes.

The selective application of a polarisation voltage between the chosen analysis electrodes and a reference electrode allows the reactant product or the probe molecules to be fixed to them. The voltage is applied to the electrodes by means of an external generator 24 connected to the addressing electrodes 14.

The probe molecules are fixed onto the analysis electrodes, for example, by means of conductive polymers of the polypyrrole or polyaniline type which are probe molecule carriers.

The chip can be subjected to several stages of electrochemical deposition by being dipped into different baths. Hence, different electrodes of the chip can be covered with different reactants, or probe molecules, sensitive to different components of the substances to be analysed.

In FIG. 2, it is to be considered that the two electrodes 12a and 12b are respectively (and successively) covered with different reactants or probe molecules 22a, 22b.

Following the lining of the electrodes with reactants or probe molecules, the chip is ready to be used to analyse a designated substance referred to as an analyte in the description that follows.

As shown in FIG. 3, the chip is disconnected from the generator and is submerged in a bath 30 containing the analyte.

This bath contains, for example, target molecules 32 which pair up with or react with the reactant or the probe molecules 22a previously deposited on the first electrode 12a. For reasons of clarity, the target molecules 32 are represented diagrammatically in a crude manner.

The target molecules 32 do not however inter-react with the second electrode 12b whose reactive coating or probe molecules are not compatible with them.

After having been removed from the bath of analyte 30, the chip is analysed so as to determine the electrodes where a reaction or a pairing up has taken place.

In the example described in FIG. 4, the chip 10 is analysed by a fluorescence detection method. Such a method is particularly suitable when the target molecules are labelled with a fluorescent labelling product called a fluophor.

However, it is also possible to envisage other methods of analysis such as electrical measurement methods using impedance measurements, measurement by microbalance, optical measurement using a change in refractive index and analytical methods using radioactive labelling.

As shown in FIG. 4, the chip assembly 10 is subjected to light radiation 40 of a first wavelength coming from a light source which has not been represented.

The labelled target molecules absorb the light radiation 40 and emit a light radiation 42 with a second characteristic wavelength which is different to the first wavelength.

A detection system 46, sensitive to the second wavelength permits the detection of the light re-emitted from the electrodes carrying the target molecules labelled by the fluorescent product. It is therefore possible, by knowing the nature of the reactants or the probe molecules previously deposited on each electrode to determine the components of the analyte which are fixed there.

A difficulty met with when carrying out the method of analysis illustrated in FIGS. 1 to 4 is associated with the large quantity of liquid required to form the bath of electrolyte (FIG. 2) and the large quantity of analyte necessary in order to submerge the chip 10 in it (FIG. 3).

Another difficulty is the placing and the withdrawal of the slices or the chips in a sample carrier. Their connection is a delicate and tedious operation which must be carried out at least twice for the lining of the electrodes and for the analysis. Furthermore, the user does not necessarily have the sample carrier equipment available and cannot envisage an individual reconfiguration of the chips through a complementary deposition of reactants other than those which were originally deposited.

There are also problems posed by the deterioration of the connector which is in contact with the slice and as a consequence with the liquid contained in the sample carrier.

The sample carrier could possibly be adapted to contain a single chip and the liquid to be analysed. However the user will note that the placing and the withdrawal of chips from the sample carrier is not very compatible with analyses carried out on a large series of chips.

Finally, when the addressing electrodes are connected to a measuring apparatus in order to carry out a qualitative analysis of components that have reacted with the electrodes on the chip, it would appear that the liquid to be analysed wets the addressing electrodes and/or the connector and risks falsifying the measurements.

DESCRIPTION OF THE INVENTION

The aim of the invention is to provide an analysis microsystem that enables one to avoid the difficulties listed above.

One aim in particular is to provide a low-cost microsystem that is easy to use and requires small quantities of electrolyte or analyte to carry out the analyses previously described.

Another aim is to provide a system that can be easily reconfigured by the user and is in a form that facilitates the analytical operations.

Finally an aim is to provide a reliable system of analysis in which the liquid to be analysed does not risk coming into contact with connectors connected to external apparatus.

To achieve these aims, the object of the invention is more precisely an analysis micro-system with an integrated cuvette that includes a chip support having at least one cuvette, at least one chip arranged in each cuvette, the chip comprising analysis electrodes and addressing electrodes, and connection means to connect the addressing electrodes to at least one electrical apparatus external to the microsystem.

Conforming to the invention, the connection means comprise connection terminals arranged on the support, outside the cuvette, and electrical links connecting the connection terminals to the addressing electrodes.

Thanks to the invention and notably because the connection terminals are situated on the support and not on the chip itself, the assembly formed by the chip and the support is highly ergonomic and permits easy connection with external apparatus. In particular, such a design allows the user to "reconfigure" a chip by once again carrying out depositions of reactants on the chips, without particular equipment being necessary and without using baths of electrolyte requiring large quantities of liquid. Furthermore, the electrolyte or analyte contained in the cuvette does not risk coming into contact with the connection terminals or the connectors of external apparatus to which they are linked.

The external electrical apparatus can either be voltage generators to apply predetermined electrical potentials to the electrodes of the chip, or electrical measurement apparatus that permits electrical values to be measured, such as the conductivity between the electrodes of the chip.

According to a particular design of the microsystem, the chip can comprise a substrate having analysis and addressing electrodes, the substrate being fixed permanently in the cuvette of the chip support.

Such a design is particularly advantageous since it allows separate large-scale manufacture of chips and of the support.

In particular, a large number of chips can be produced collectively on a single slice of semiconductor which is eventually cut up. The chips are then individually integrated with a support in order to constitute an analysis microsystem conforming to the invention.

According to another design, the chip can be directly produced in a chip support. Hence the chip support also constitutes a support substrate for the analysis and the addressing electrodes.

According to other aspects of the invention, the microsystem can comprise means of heating the chip which are integrated under the chip, either directly in the substrate of the chip or in the chip support.

These heating means, possibly associated with a thermocouple that allows one to check and control precisely the temperatures for deposition of reactants or analysis temperatures on the electrodes.

According to another advantageous aspect, the size and the volume of the cuvette can be adjusted in relation to the chip which is housed in it and the applications envisaged. Hence an exact quantity of electrolyte or analyte is contained in the cuvette.

Conforming to one particular embodiment of the chip support, this can comprise a first substrate forming a cuvette bottom and a second substrate arranged on the first substrate and forming the side walls of the cuvette.

According to a variant, the cuvette can also be etched directly in a massive substrate.

Other characteristics and advantages of the invention will better emerge from the description which follows, that refers to the Figures in the appended drawings. This description is given for purely illustrative purposes and is not limitative.

DETAILED DESCRIPTION OF EMBODIMENTS OF THE INVENTION

An analysis micro-system conforming to the invention can comprise several cuvettes containing electronic chips.

However, according to a preferred embodiment, each micro-system only has a single cuvette with a single chip.

Figure 1:
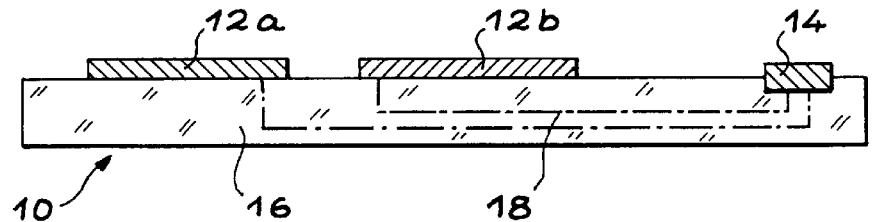
FIG. 1, already described, is a diagrammatic cross section of a biological sensor chip.
Figure 2:
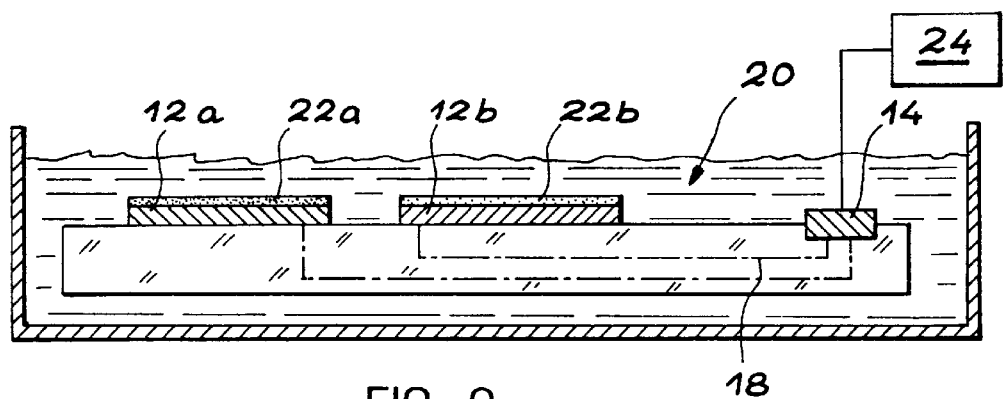
FIG. 2, already described, is a diagrammatic cross section of the chip in FIG. 1 immersed in a bath of electrolyte.
Figure 3:
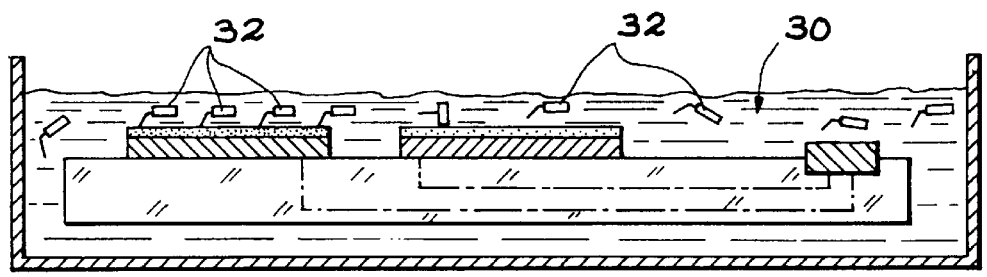
FIG. 3, already described, is a diagrammatic cross section of the chip in FIG. 1 immersed in a bath of analyte.
Figure 4:
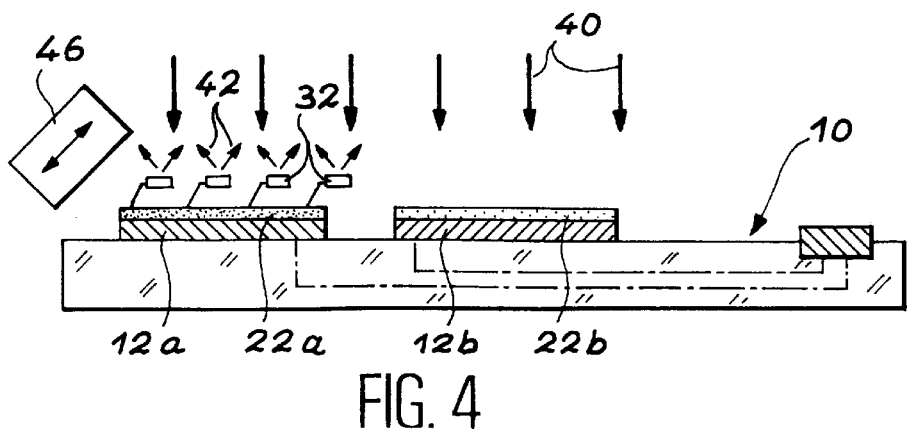
FIG. 4, already described, is a diagrammatic cross section of the chip in FIG. 1 subjected to an analysis by fluorescence.
Figure 5:
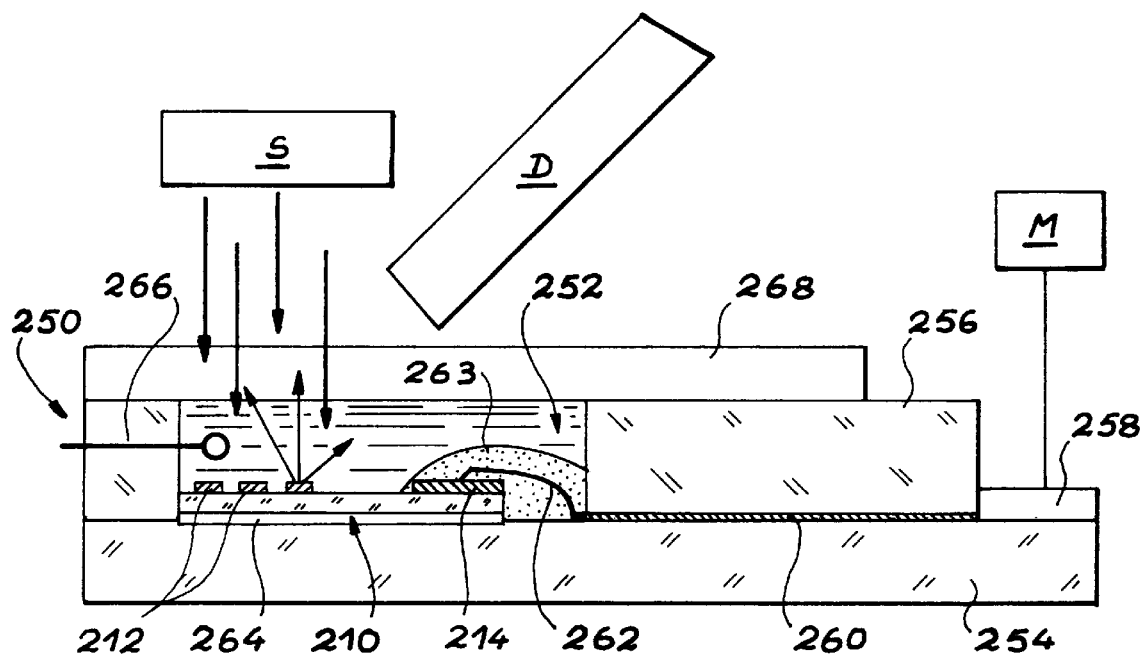
FIG. 5 is a diagrammatic cross section of an analysis micro-system for liquids conforming to the invention.

Hence, the analysis micro-system shown in FIG. 5 includes a chip support 250 having a single cuvette 252. The cuvette 252 contains an electronic chip 210, such as, for example, a biological or chemical sensor chip.

The chip support 250 essentially comprises a first substrate 254 forming a cuvette bottom and a second substrate 256 attached (for example by sticking) to the first substrate and defining the side wall or side walls of the cuvette.

The first and second substrates are preferably electrically insulating substrates made of a material such as a glass fiber/epoxy resin composite material.

The first substrate 254 comprises at one end situated outside the cuvette a set of connection terminals 258. The terminals 258, separated from the cuvette by the second substrate, are electrically linked to the addressing electrodes 214 of the chip 210 arranged in the cuvette 252. The electrical link between the terminals and the addressing electrodes is produced, for example, by conducting tracks 260, passing between the first and second substrates, and through connecting wires 262 linking the conducting tracks 260 to the corresponding addressing electrodes 214.

In order to protect and to insulate the addressing electrodes 214 and the connecting wires 262 from liquids poured into the cuvette 252, they are encased, for example, in an insulating layer 263 of polymer material.

Reference number 264 indicates a heating resistance arranged under the chip 214. This resistance, which can be electrically supplied from outside the support, allows the temperature of the chip 210 and the analysis electrodes 212 of the chip to be controlled.

The control of the temperature can be carried out by a thermocouple 266 that extends into the cuvette in order to measure the temperature of a liquid that it contains.

The cuvette 252 of the support can be filled with an electrolyte or a solution containing probe molecules so as to line the analysis electrodes 212 of the chip in the manner previously described.

When this operation is completed, the electrolyte can be replaced by the analyte.

Advantageously, a cover 268 supported on the second substrate 256 can be provided to hermetically close the cuvette 252 and to preserve the analyte during its analysis. This feature facilitates the manipulation of the micro-system.

When the analysis method is a method of fluorescence measurement such as the one previously described, the cover 268 can advantageously be constituted by a sheet of glass which allows incident radiation coming from a light source S to pass through it and allows the fluorescence radiation to pass to a detector D.

The analysis of the properties or the composition of the analyte can also be carried out by electrical conductivity measurements by connecting a suitable measuring apparatus M to the connection terminals 258.

Figure 6:
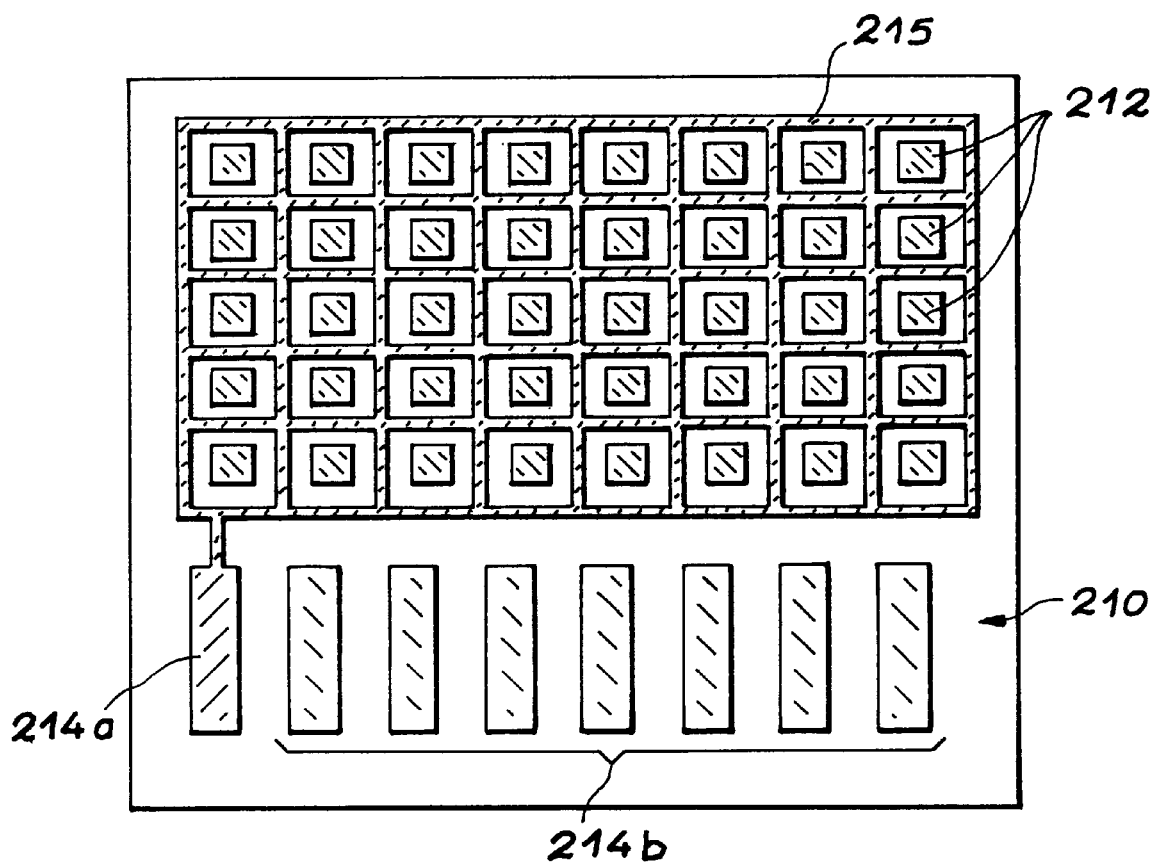
FIG. 6 is a view from above, on a larger scale, of a chip that is able to be integrated into the analysis micro-system in FIG. 5.

FIG. 6 shows an example of a chip 210 that can be used in the micro-system of the invention.

The chip 210 comprises, on a substrate, a plurality of analysis electrodes 212, arranged in lines and in columns, and possibly a counter-electrode 215 in the form of a grid surrounding the analysis electrodes. The analysis electrodes 212 and the counter electrode are made of a material such as gold or platinum for example.

The chip also comprises a plurality of addressing electrodes of which a first addressing electrode 214a is directly connected to the counter electrode 215. The other addressing electrodes 214b are connected to the analysis electrodes 212, for example when the number of electrodes is large, by means of a multiplexer-demultiplexer integrated into the chip and not represented in the Figure.

In order to line an analysis electrode with a reactant by electro-deposition, a voltage is applied between this electrode and the counter electrode by appropriate addressing of the addressing electrodes.

In the same way, during an analysis stage, a measurement current can be selectively measured between a given analysis electrode and the counter electrode.

The chip in FIG. 6 can be permanently fixed in the chip support 250 previously described (FIG. 5), for example, by sticking the substrate of the chip 210 into the bottom of the cuvette, via a surface that does not include electrodes.

Figure 7:
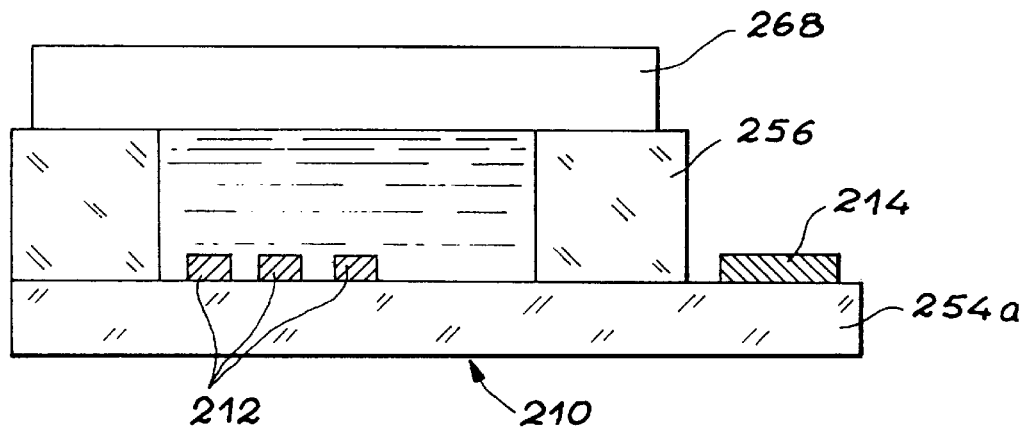
FIG. 7 is a diagrammatic cross section of an analysis micro-system for liquids conforming to the invention and constituting a variant of the microsystem in FIG. 5.

FIG. 7 shows another embodiment of the micro-system of the invention, constituting a variant of the embodiment described above.

According to this variant, the chip 210 comprises a substrate 254a which is not stuck into the bottom of the cuvette, but which directly constitutes the first substrate and which therefore forms the bottom of the cuvette.

Hence, the second substrate 256, which defines the side walls of the cuvette and which is attached to the substrate 254a, is in fact directly attached onto the chip 210.

Through analogy with FIG. 5, the reference numbers 212, 214 and 268 respectively designate the analysis electrodes, the addressing electrodes and the cover of the cuvette.

What is claimed is:

1. An analysis micro-system with integrated cuvette comprising:
   (a) a chip support having at least one cuvette having a bottom and side walls, said chip support comprising (1) a first substrate forming said cuvette bottom and (2) a second substrate arranged on the first substrate and forming said side walls;
   (b) at least one chip comprising analysis electrodes and addressing electrodes, said chip being positioned in said cuvette; and
   (c) connection means to connect the addressing electrodes to at least one electrical apparatus external to the micro-system, said connection means comprising connection terminals arranged on said support outside said cuvette, and electrical links connecting said connection terminals to said addressing electrodes, said links arranged such that they pass between the first and second substrates.

2. A micro-system according to claim 1, in which the chip comprises a further substrate having said analysis and addressing electrodes, said further substrate being permanently fixed in the cuvette.

3. A micro-system according to claim 1, in which the chip is produced directly on the chip support.

4. A micro-system according to claim 1, comprising means for heating the chip.

5. A micro-system according to claim 4, in which the heating means comprise an electrical resistance integrated into the chip.

6. A micro-system according to claim 4, in which the heating means comprise an electrical resistance positioned under the chip.

7. A micro-system according to claim 1, in which the chip support comprises a thermocouple.

8. A micro-system according to claim 1, in which the addressing electrodes and the electrical links are insulated by an insulating encapsulation.

9. A micro-system according to claim 1 in which the cuvette has a volume determined in relation to a quantity of liquid required by the chip for processing.

10. A micro-system according to claim 1, including a sheet of glass arranged on the second substrate and covering the cuvette.

11. A micro-system according to claim 1, in which the support comprises a bulk substrate in which the cuvette is formed.

* * * * *